United States Patent [19]
Kavanagh et al.

[11] Patent No.: US 6,206,864 B1
[45] Date of Patent: Mar. 27, 2001

(54) OSTOMY APPLIANCE WITH INVERTED TRIANGULAR FACEPLATE AND NON-PROTRUDING PULL TABS

(75) Inventors: Seamus T. Kavanagh, Co. Mayo (IE); Robert T. Dixon, Cambridgeshire (GB); Garrett B. McGuinness, Sligo (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 09/440,918

(22) Filed: Nov. 16, 1999

(51) Int. Cl.$^7$ ......................................................... A61F 5/44
(52) U.S. Cl. .................................................................. 604/332
(58) Field of Search ................................... 604/333, 339, 604/343, 176, 335, 338, 342, 344, 345

(56) References Cited

U.S. PATENT DOCUMENTS

| | | | |
|---|---|---|---|
| 4,213,458 | 7/1980 | Nolan et al. | 128/283 |
| 4,231,369 | 11/1980 | Sorensen et al. | 128/283 |
| 4,551,490 | 11/1985 | Doyle et al. | 524/22 |
| 4,596,566 | * 6/1986 | Kay | 604/343 |
| 5,074,851 | * 12/1991 | Plass et al. | 604/333 |
| 5,125,133 | 6/1992 | Morrison | 24/30.5 |
| 5,403,299 | 4/1995 | Schneider | 604/332 |
| 5,492,943 | 2/1996 | Stempel | 523/111 |
| 5,578,023 | 11/1996 | Schneider | 604/332 |
| 5,607,413 | 3/1997 | Holmberg et al. | 604/342 |
| 5,811,116 | * 9/1998 | Gilman et al. | 424/443 |
| 5,902,295 | * 5/1999 | Steer et al. | 604/449 |

* cited by examiner

Primary Examiner—Sharon Kennedy
Assistant Examiner—Ann Y. Lam
(74) Attorney, Agent, or Firm—Tilton, Fallon Lungmus

(57) ABSTRACT

An ostomy appliance is disclosed in which the adhesive faceplate for holding the appliance in place is of inverted triangular shape with rounded corners. The faceplate includes an adhesive layer composed of a hydrocolloid-containing pressure-sensitive adhesive, a protective release sheet removably covering the bodyside surface of the adhesive layer, and a flexible backing layer covering the opposite (pouchside) surface of the adhesive layer and permanently securing the faceplate to an ostomy pouch about the perimeter of a stoma-receiving opening. Because of its orientation, the triangular faceplate has one of its side edges extending across the upper end of the pouch (i.e., facing upwardly when the pouch is worn), resulting in a construction in which the area of the faceplate's adhesive layer is wider above the faceplate's opening than below it. In a preferred embodiment, the adhesive layer is recessed or set back at one of the faceplate's upper corners to provide both the release sheet and backing layer with non-protruding tab portions that facilitate both application and removal of the appliance.

5 Claims, 1 Drawing Sheet

OSTOMY APPLIANCE WITH INVERTED TRIANGULAR FACEPLATE AND NON-PROTRUDING PULL TABS

BACKGROUND AND SUMMARY

Conventional one-piece ostomy appliances, and the pouch components of two-piece adhesively-coupled appliances, generally consist of collection pouches equipped with adhesive faceplates of various shapes for adhering the appliances to the peristomal skin surfaces of patients or to the attachment surfaces of mounting rings adhesively secured to such peristomal surfaces. Most commonly, the faceplates have outer margins that are either generally round or square (with rounded corners) as shown, for example, in U.S. Pat. Nos. 5,403,299 and 4,213,458, although faceplates having other outlines are also known (see, for example, U.S. Pat. No. 5,811,116). Regardless of its shape, such a faceplate essentially consists of an adhesive layer, preferably of a hydrocolloid-containing adhesive capable of absorbing moisture and having both wet and dry tack, and a backing layer of polymeric film or fabric covering the backside (pouchside) surface of the adhesive layer and securing the faceplate and pouch together about the stoma-receiving openings of the respective parts. In addition, a typical pouch faceplate assembly is supplied to the user with a removable release sheet that covers the bodyside surface of the faceplate's adhesive layer. To facilitate removal of the release sheet at the time of application, such a sheet is commonly provided with a tab portion that projects away from the periphery of the adhesive layer. In addition, the backing layer may also be provided with an outwardly projecting tab portion to assist a user in peeling the faceplate away from the skin (or from the attachment surface of a mounting ring) when removal of an appliance is desired (see U.S. Pat. Nos. 5,578,023 and 5,607,413).

Where provided, such pull tabs almost always project upwardly, that is, towards the upper ends of the pouches, to render them more readily accessible in use, but such a location has offsetting disadvantages. Because of manufacturing requirements, the perimeter of a faceplate (including its tab portion) must necessarily be spaced inwardly from the periphery of the pouch on which the faceplate is mounted, with the result that a faceplate having upwardly protruding tabs must be located lower along the pouch wall than if such tabs were omitted. For any given size of pouch, that means that the provision of upwardly-projecting tabs reduces the effective volumetric capacity of the pouch. Also, the tab for a backing layer that extends upwardly away from the remainder of the faceplate may be exposed for possible contact with clothing and present the risk that such contact might initiate unintentional detachment of the faceplate from the skin.

It is therefore a main aspect of this invention to provide an ostomy appliance having an adhesive faceplate shaped and oriented to provide more effective adhesive attachment where it is needed most in resisting pulling forces in use, while reducing the area of adhesive attachment in the lower region of a faceplate where excessive contact might cause pinching and other patient discomforts. More specifically, the faceplate of the appliance is of inverted triangular shape having rounded corners, with one of the corners facing downwardly towards the lower end of the pouch and one of its side edges facing upwardly along the upper end of the pouch. The result is an appliance having a faceplate of greater width in its upper region (i.e., above the midpoint of its stoma-receiving opening) than in its lower region, thereby providing greater adhesion where it is needed most, reducing the size of the faceplate in its lower region to promote greater patient comfort, and also limiting material volume and expense (recognizing that hydrocolloid-containing adhesive compositions constitute a significant portion of the cost of such appliances).

Two of the rounded corners of the faceplate therefore face upwardly and outwardly and, in a preferred embodiment, both the removable release sheet and the backing layer of the symmetrical faceplate have non-protruding pull tabs along one of those corners. At such corner, the adhesive layer is set back or recessed to create a marginal corner area where the coextensive release sheet and backing layer, while following the regular marginal contour of the faceplate, have no adhesive material between them. Such adhesive-free portions therefore serve as pull tabs to facilitate removal of the release sheet at the time of application of the appliance as well as initiating detachment of the faceplate from the skin when removal is desired. Since the tabs are non-protruding—and especially because they are non-protruding in an upward direction—they do not interfere with close positioning of the faceplate to the upper margin of the pouch, thereby optimizing pouch volume. The fact that the tabs are non-protruding is also believed to reduce the possibility that movement of clothing or contact with other objects might initiate unintended detachment of the upper portion of the faceplate from the skin.

While the provision of such non-protruding tabs reduces the adhesive material that would otherwise be available for contact with the skin (or with the attachment surface of a mounting ring adhesively secured to the skin), the inverted triangular shape of the faceplate nevertheless assures that the adhesive surface in the upper region of the faceplate (i.e., above the midpoint of the faceplate opening) has greater width than in the faceplate's lower region and provides a substantial area of adhesion above and to the sides of the faceplate opening. Thus, the configuration and orientation of the faceplate optimize patient security while at the same time allowing for the provision of pull tabs along a portion of the upper margin of such a faceplate.

Other features, objects and advantages of the invention will become apparent from the specification and drawings.

DRAWINGS

DETAILED DESCRIPTION OF PREFERRED EMBODIMENT

Figure 1:
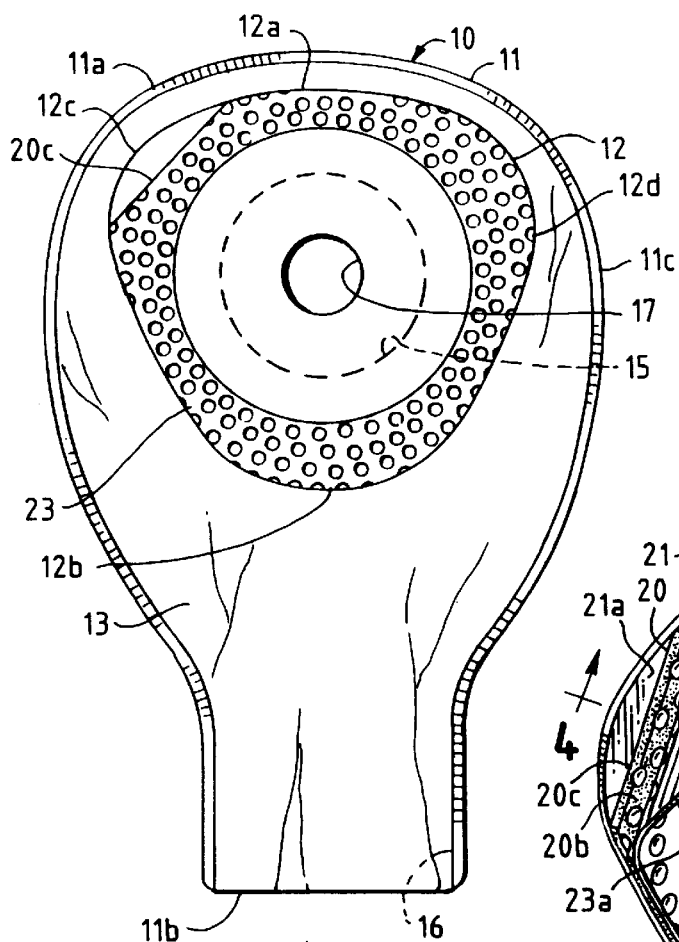
FIG. 1 is an elevational view of an ostomy appliance embodying the invention.

Referring to the drawings, the numeral 10 designates an ostomy appliance consisting essentially of a pouch 11 and a faceplate 12. The drawings depict what may be referred to as a one-piece appliance, such term being commonly used to mean a unitary appliance having a faceplate intended to be adhesively secured directly to the peristomal skin surfaces of a wearer. It is to be noted, however, that at least some of the advantages of this invention might be obtained if used in a two-piece appliance in which the pouch and its adhesive faceplate are intended to be adhesively attached to (and detached from) the surface of a mounting ring which in turn is adhesively attached to such peristomal skin surfaces. Therefore, the term "appliance," as here used is meant to include not only a one-piece ostomy appliance but also the pouch/faceplate component of a two-piece adhesively-coupled appliance.

Pouch 11 has upper and lower ends 11a and 11b, respectively and is typically composed of two panels or walls 13 and 14 of liquid and gas impermeable thermoplastic material heat sealed or otherwise secured together along their marginal edges 11c. One wall 13 (the bodyside wall) has a stoma-receiving opening 15 located in the upper portion of the pouch. The pouch as shown is of the drainable type with an opening 16 at its lower end that may be closed by means of a suitable clamping device such as, for example, the clamp shown and described in U.S. Pat. No. 5,125,133. Alternatively, a pouch may be provided at its lower end with a suitable drain valve, especially if the pouch is intended for use as a urostomy appliance, or may be completely closed at its lower end as, for example, a colostomy pouch. It is to be understood that the symmetrical shape of the pouch as shown is not critical and that other pouch shapes commonly available and widely known in the art may be utilized. In addition, one or both outer surfaces of the pouch may be covered with soft, porous non-woven fabrics (not shown) to enhance patient comfort and reduce sound, all as known in the art.

As shown in FIG. 1, faceplate 12 has the general shape of an inverted equilateral triangle with rounded corners. The faceplate is oriented so that one of its sides 12a faces upwardly, extending along and slightly below the upper edge portion 11a of the pouch. The opposing corner 12b faces downwardly towards the pouch's lower end 11b, and side corners 12c and 12d face upwardly and outwardly. A centrally-located opening 17 extends through the faceplate and is concentric with the opening 15 in wall 13 of the pouch. In the embodiment illustrated, opening 17 is a starter opening that may be cut with scissors to a larger size that matches the size and shape of a patient's stoma.

The thin, flat faceplate comprises an adhesive layer 20 having pouchside and bodyside surfaces 20a and 20b, respectively. Most advantageously, the adhesive layer is formed of a soft, skinfriendly hydrocolloid-containing adhesive material that is capable of absorbing moisture and has both wet and dry tack. Such a material is commonly referred to as a skin barrier composition and typically comprises a continuous elastomeric adhesive phase having hydrocolloid particles dispersed throughout the continuous phase. Initial tack, usually referred to as "dry tack," is provided by the continuous phase but, because such a composition is occlusive or non-breathable, adherence to the skin would be disrupted by perspiration and by liquid stomal discharge if it were not for the dispersed hydrocolloids which absorb fluids and thereby maintain and possibly enhance adhesive attachment to the skin. U.S. Pat. No. 4,551,490 and other references identified therein disclose that suitable water-absorbing and swellable hydrocolloid gums may include sodium carboxymethylcellulose, pectin, gelatin, guar gum, locust bean gum, and the like. The elastomers used in the continuous phase may be polyisobutylene, natural rubber, silicone rubber, acrylnitrile rubber, and other elastomers known in the art to have similar properties. For flow resistance, shape-recoverability, and the capacity to retain integrity during swelling of the hydrocolloid component upon liquid absorption, the continuous phase may include a physically crosslinked elastomer such as a styrene-olefin-styrene block copolymer as disclosed in co-owned U.S. Pat. No. 5,492,943, the disclosure of which is incorporated by reference herein. A composition of that patent includes a blend of two viscoelastic adhesive elastomers, specifically high molecular weight polyisobutylene and a styrene block copolymer which, along with a plasticizer (preferably petrolatum) and a suitable tackifier and antioxidant, form a continuous phase in which the hydrocolloid particles such as sodium carboxymethylcellulose and pectin are dispersed. It is believed that other barrier compositions, also containing physically crosslinked elastomers or mixtures of such elastomers, such as those disclosed in U.S. Pat. No. 4,231,369, may also be used.

Figure 2:
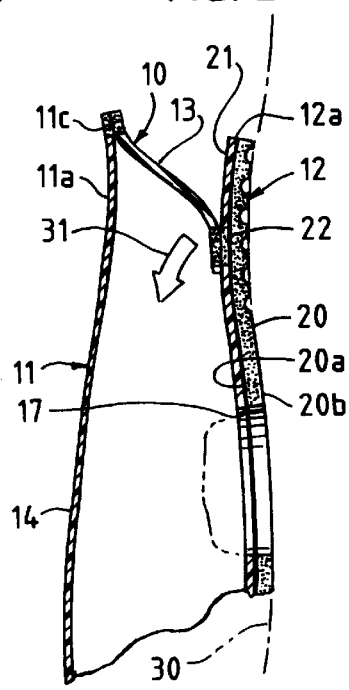
FIG. 2 is a fragmentary vertical sectional view schematically depicting the application of forces when such an appliance is in use.

The faceplate also includes a backing layer 21 covering all or most of the pouchside surface 20a of adhesive layer 20. The backing layer should be flexible and heat-sealable so that it may be permanently joined to pouch wall 13 by annular heat seal 22 extending around the stoma-receiving opening 15 of the pouch (FIG. 2). The backing layer may be in the form of a thermoplastic film such as polyethylene or other polyolefin and an elastomeric film, such as polyurethane or an ethylene methacrylate copolymer, is believed particularly suitable. Alternatively, the backing layer may be formed of a heat sealable fabric, such as a porous non-woven polyolefin or other heat-sealable fabrics having similar properties. It is also to be understood that, if desired, the backing layer 21 may be composed of two or more sub-layers with each sub-layer providing properties contributing to those of the backing layer as a whole.

The bodyside surface 20b of the faceplate's adhesive layer 20 is covered by a removable release sheet 23 formed of a flexible but generally non-stretchable material such as siliconized paper or a siliconized polymeric material such as polyethylene terephthalate. Preferably the release sheet and the underlying surface of the adhesive layer 20 are dimpled or embossed, at least in their outer portions as shown in the drawings, although such dimpling or embossing may be omitted if desired. The purposes and advantages of such dimpling or embossing are disclosed in co-owned U.S. Pat. No. 5,811,116, the disclosure of which is incorporated by reference herein.

In a preferred embodiment, the adhesive layer 20 is recessed or relieved at one of the upper corners of the faceplate to provide an edge 20c set back from the edges of the release sheet 23 and backing layer 21. The setback results in corner portions 23a and 21a constituting tab portions that are non-protruding to the extent that they do not alter the rounded triangular contour of the faceplate as a whole.

Figure 3:
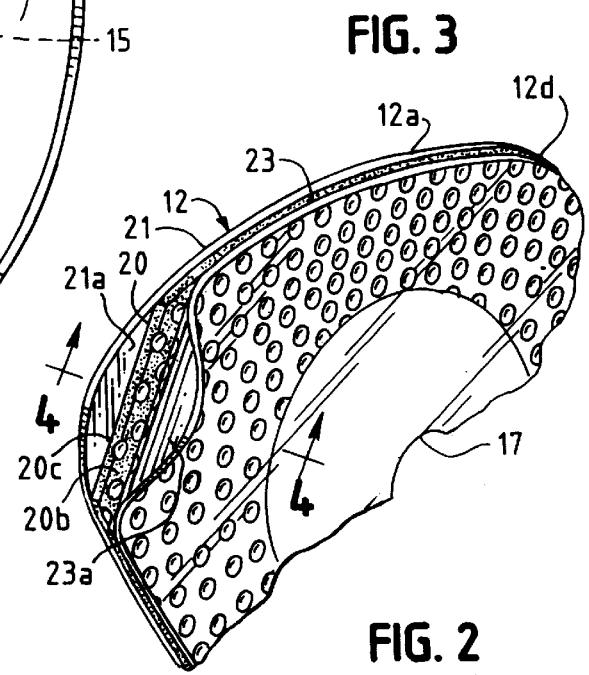
FIG. 3 is a fragmentary perspective view showing the pull tabs at an upper corner of the appliance's faceplate (the pouch is omitted for clarity of illustration).
Figure 4:
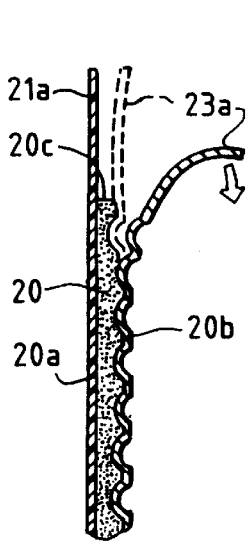
FIG. 4 is an enlarged sectional view taken along line 4—4 of FIG. 3.

In use of the appliance, the pull tab 23a of release sheet 23 is gripped between the fingers and the sheet is peeled away to expose the bodyside 20b surface of adhesive layer 20 (FIGS. 3 and 4). The faceplate is then adhered to the peristomal skin surfaces 30 of a wearer with the pouch generally oriented as shown in FIGS. 1 and 2. During subsequent use, as the pouch becomes filled with liquid/solid waste, downward forces tend to be exerted in the general direction of arrow 31 (FIG. 2) but such downward pulling forces may be effectively resisted because of the inverted triangular shape of the faceplate and the relatively large area and wide extent of the upper adhesive surface of the faceplate.

Figure 5:
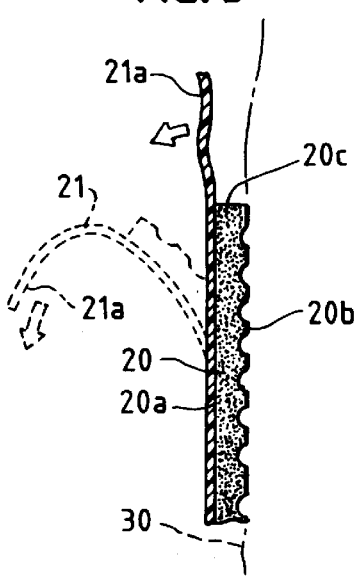
FIG. 5 is a sectional view similar to FIG. 4 but illustrating use of the pull tab of the faceplate's backing layer.

When removal of the appliance is desired, a user simply grips tab 21a of the backing layer 21 and peels the faceplate away from skin surfaces 30 as depicted in FIG. 5.

While in the foregoing, we have disclosed an embodiment of the invention in considerable detail for puposes of illustration, it will be understood by those skilled in the art that many of these details may be varied without departing from the spirit and scope of the invention.

What is claimed is:

1. An ostomy appliance comprising a collection pouch having upper and lower ends and including front and rear walls joined together along their outer margins; one of said walls having a stoma-receiving opening located adjacent said upper end of said pouch; and an adhesive faceplate for securing said appliance to the peristomal skin surfaces of a wearer; said faceplate being generally triangular in outline with rounded corners and being oriented with one side edge and two corners thereof facing upwardly; said faceplate including an adhesive layer composed of a hydrocolloid-containing pressure-sensitive adhesive having pouchside and bodyside surfaces, a removable release sheet covering said bodyside surface, and a flexible backing layer affixed to said pouchside surface; said faceplate having a generally central opening therethrough aligned with said opening of said pouch and having said backing layer secured to said pouch about said pouch opening; said backing layer and said release sheet extending beyond said adhesive layer at one of said upwardly-facing corners of said faceplate to provide finger tabs for use in removing said release sheet from said bodyside surface and later in removing said faceplate from the peristomal skin surfaces of a wearer.

2. The ostomy appliance of claim 1 in which said faceplate has the general outline of an equilateral triangle with rounded corners.

3. The ostomy appliance of claim 1 in which said one side edge of said faceplate extends generally horizontally when said appliance is worn by a wearer in standing position.

4. The ostomy appliance of claim 1 in which said triangular faceplate is symmetrical in outline.

5. An adhesive faceplate for an ostomy pouch, said faceplate having the general shape of an equilateral triangle with rounded corners and having a central opening extending therethrough; said faceplate including an adhesive layer composed of a hydrocolloid-containing pressure-sensitive adhesive having pouchside and bodyside surfaces, a removable release sheet covering said bodyside surface, and a flexible backing layer over said pouchside surface; said backing layer and release sheet extending beyond said adhesive layer at one of said rounded corners of said faceplate to provide said release sheet with a non-protruding finger-gripping tab for use in removing said release sheet from said bodyside surface and also providing said backing layer with a non-protruding finger-gripping tab for use in removing said faceplate from its adhesive attachment to the peristomal skin surfaces of a wearer.

\* \* \* \* \*